United States Patent
Jacobsen et al.

(10) Patent No.: US 9,144,664 B2
(45) Date of Patent: Sep. 29, 2015

(54) METHOD AND APPARATUS FOR MANIPULATING MOVEMENT OF A MICRO-CATHETER

(75) Inventors: Stephen C. Jacobsen, Salt Lake City, UT (US); Fraser M. Smith, Salt Lake City, UT (US)

(73) Assignee: Sarcos LC, Salt Lake City, UT (US)

( * ) Notice: Subject to any disclaimer, the term of this patent is extended or adjusted under 35 U.S.C. 154(b) by 611 days.

(21) Appl. No.: 12/896,732

(22) Filed: Oct. 1, 2010

(65) Prior Publication Data
US 2011/0245765 A1    Oct. 6, 2011

Related U.S. Application Data

(60) Provisional application No. 61/247,886, filed on Oct. 1, 2009.

(51) Int. Cl.
*A61M 25/092* (2006.01)
*A61M 25/01* (2006.01)
(Continued)

(52) U.S. Cl.
CPC ........... *A61M 25/0102* (2013.01); *A61B 1/05* (2013.01); *A61B 1/3137* (2013.01); *A61M 25/0138* (2013.01); *A61M 25/0155* (2013.01); *A61B 1/015* (2013.01); *A61B 1/055* (2013.01); *A61M 2025/0042* (2013.01)

(58) Field of Classification Search
CPC ............... A61M 25/0122; A61M 25/0043; A61M 25/003; A61M 25/0105; A61B 2019/2211; A61B 1/00156
USPC ............. 604/95.01, 500, 95.02, 43, 264, 528, 604/122
See application file for complete search history.

(56) References Cited

U.S. PATENT DOCUMENTS 3,817,635 A    6/1974 Kawahar
3,856,000 A   12/1974 Chikama
(Continued)

FOREIGN PATENT DOCUMENTS

CN    1481753    3/2004
DE    197 42 973   4/1998
(Continued)

OTHER PUBLICATIONS

Boppart, S.A. et al., "Forward-imaging instruments for optical coherence tomography." Optics Letters, Nov. 1, 1997, vol. 22, No. 21, pp. 1618-1620.
(Continued)

*Primary Examiner* — Laura Bouchelle
(74) *Attorney, Agent, or Firm* — Thorpe North & Western, LLP (57) ABSTRACT

A medical device and method for manipulating movement of a micro-catheter, the device comprising an elongated tubular member having at least one lumen therein, wherein the lumen is proximally coupled to a pressurized fluid control system configured to regulate fluid flow through the elongated tubular member. An aperture is disposed near a distal end of the elongated tubular member, the aperture being in fluid communication with the at least one lumen. In one aspect, the aperture is oriented at an angle which is non parallel to the longitudinal axis of the elongated tubular member. A nozzle is coupled to the aperture, wherein the nozzle is configured to regulate pressurized flow out of the catheter to manipulate movement of the distal end of the elongated tubular member.

13 Claims, 4 Drawing Sheets

(51) Int. Cl.
*A61B 1/05* (2006.01)
*A61B 1/313* (2006.01)
A61B 1/015 (2006.01)
A61B 1/055 (2006.01)
A61M 25/00 (2006.01)

(56) References Cited

U.S. PATENT DOCUMENTS

| | | | |
|---|---|---|---|
| 3,886,933 A | 6/1975 | Mori et al. | |
| 3,918,438 A | 11/1975 | Hayamizu et al. | |
| 3,971,065 A | 7/1976 | Bayer | |
| 4,277,168 A | 7/1981 | Oku | |
| 4,283,115 A | 8/1981 | Fraissl | |
| 4,349,456 A | 9/1982 | Sowman | |
| 4,360,275 A | 11/1982 | Louderback | |
| 4,403,985 A * | 9/1983 | Boretos | 604/528 |
| 4,475,902 A * | 10/1984 | Schubert | 604/95.02 |
| 4,487,206 A | 12/1984 | Aagard | |
| 4,491,865 A | 1/1985 | Danna et al. | |
| 4,515,444 A | 5/1985 | Prescott et al. | |
| 4,573,450 A | 3/1986 | Arakawa | |
| 4,585,349 A | 4/1986 | Gross et al. | |
| 4,588,294 A | 5/1986 | Siegmund | |
| 4,589,404 A | 5/1986 | Barath et al. | |
| 4,593,313 A | 6/1986 | Nagasaki et al. | |
| 4,594,613 A | 6/1986 | Shinbori et al. | |
| 4,600,831 A | 7/1986 | Hutley | |
| 4,604,992 A | 8/1986 | Sato | |
| 4,620,534 A | 11/1986 | Zartman | |
| 4,621,284 A | 11/1986 | Nishioka et al. | |
| 4,622,954 A | 11/1986 | Arakawa et al. | |
| 4,626,079 A | 12/1986 | Nakamura et al. | |
| 4,641,927 A | 2/1987 | Prescott et al. | |
| 4,646,724 A | 3/1987 | Sato et al. | |
| 4,672,218 A | 6/1987 | Chrisman et al. | |
| 4,706,118 A | 11/1987 | Kato et al. | |
| 4,707,134 A | 11/1987 | McLachlan et al. | |
| 4,723,843 A | 2/1988 | Zobel | |
| 4,725,721 A | 2/1988 | Nakamura | |
| 4,745,470 A | 5/1988 | Yabe et al. | |
| 4,745,471 A | 5/1988 | Takamura et al. | |
| 4,783,591 A | 11/1988 | Sullivan | |
| 4,785,815 A | 11/1988 | Cohen | |
| 4,790,624 A | 12/1988 | Van Hoye et al. | |
| 4,791,479 A | 12/1988 | Ogiu et al. | |
| 4,802,487 A | 2/1989 | Martin et al. | |
| 4,803,562 A | 2/1989 | Eino | |
| 4,832,003 A | 5/1989 | Yabe | |
| 4,843,416 A | 6/1989 | Brower | |
| 4,846,785 A | 7/1989 | Cassou et al. | |
| 4,859,040 A | 8/1989 | Kitagishi et al. | |
| 4,867,137 A | 9/1989 | Takahashi | |
| 4,867,138 A | 9/1989 | Kubota et al. | |
| 4,867,174 A | 9/1989 | Skribiski | |
| 4,880,298 A | 11/1989 | Takada | |
| 4,895,138 A | 1/1990 | Yabe | |
| 4,916,534 A | 4/1990 | Takhashi et al. | |
| 4,926,257 A | 5/1990 | Miyazaki | |
| 4,930,880 A | 6/1990 | Miyauchi | |
| 4,932,394 A | 6/1990 | Nanaumi | |
| 4,934,340 A | 6/1990 | Ebling et al. | |
| 4,941,457 A | 7/1990 | Hasegawa | |
| 4,998,807 A | 3/1991 | Uzawa et al. | |
| 5,006,928 A | 4/1991 | Kawajiri et al. | |
| 5,009,483 A | 4/1991 | Rockwell, III | |
| 5,021,888 A | 6/1991 | Kondou et al. | |
| 5,022,972 A | 6/1991 | David et al. | |
| 5,032,913 A | 7/1991 | Hattori et al. | |
| 5,040,069 A | 8/1991 | Matsumoto et al. | |
| 5,061,036 A | 10/1991 | Gordon | |
| 5,093,719 A | 3/1992 | Prescott | |
| 5,105,269 A | 4/1992 | Nakamura et al. | |
| 5,106,387 A | 4/1992 | Kittrell et al. | |
| 5,109,859 A | 5/1992 | Jenkins | |
| 5,111,804 A | 5/1992 | Funakoshi | |
| 5,113,254 A | 5/1992 | Kanno et al. | |
| 5,121,213 A | 6/1992 | Nishioka | |
| 5,126,639 A | 6/1992 | Srivastava | |
| 5,130,804 A | 7/1992 | Tamura et al. | |
| 5,165,063 A | 11/1992 | Strater et al. | |
| 5,166,656 A | 11/1992 | Badehi et al. | |
| 5,182,672 A | 1/1993 | Mukai et al. | |
| 5,188,093 A | 2/1993 | Lafferty et al. | |
| 5,190,523 A | 3/1993 | Lindmayer | |
| 5,191,203 A | 3/1993 | McKinley | |
| 5,198,894 A | 3/1993 | Hicks | |
| 5,209,219 A | 5/1993 | Hollobaugh | |
| 5,220,198 A | 6/1993 | Tsuji | |
| 5,222,477 A | 6/1993 | Lia | |
| 5,228,430 A | 7/1993 | Sakamoto | |
| 5,258,834 A | 11/1993 | Tsuji et al. | |
| 5,289,434 A | 2/1994 | Berni | |
| 5,290,555 A | 3/1994 | Guthauser et al. | |
| 5,291,010 A | 3/1994 | Tsuji | |
| 5,298,741 A | 3/1994 | Walt et al. | |
| 5,304,173 A | 4/1994 | Kittrell et al. | |
| 5,305,098 A | 4/1994 | Matsunaka et al. | |
| 5,318,024 A | 6/1994 | Kittrell et al. | |
| 5,361,166 A | 11/1994 | Atkinson et al. | |
| 5,365,268 A | 11/1994 | Minami | |
| 5,376,960 A | 12/1994 | Wurster | |
| 5,377,047 A | 12/1994 | Broome et al. | |
| 5,381,784 A | 1/1995 | Adair | |
| 5,396,366 A | 3/1995 | Brown et al. | |
| 5,398,685 A | 3/1995 | Wilk et al. | |
| 5,402,769 A | 4/1995 | Tsuji | |
| 5,408,999 A | 4/1995 | Singh et al. | |
| 5,430,475 A | 7/1995 | Goto et al. | |
| 5,434,615 A | 7/1995 | Matumoto | |
| 5,436,655 A | 7/1995 | Hiyagi et al. | |
| 5,438,975 A | 8/1995 | Miyagi et al. | |
| 5,440,669 A | 8/1995 | Rakuljie et al. | |
| 5,450,243 A | 9/1995 | Nishioka | |
| 5,455,455 A | 10/1995 | Badehi | |
| 5,458,612 A | 10/1995 | Chin | |
| 5,459,570 A | 10/1995 | Swanson et al. | |
| 5,469,841 A | 11/1995 | Kobayashi et al. | |
| 5,494,483 A | 2/1996 | Adair | |
| 5,512,940 A | 4/1996 | Takasugi et al. | |
| 5,517,997 A | 5/1996 | Fontenot | |
| 5,531,664 A | 7/1996 | Adachi et al. | |
| 5,547,455 A | 8/1996 | McKenna et al. | |
| 5,547,906 A | 8/1996 | Badehi | |
| 5,594,497 A | 1/1997 | Ahern | |
| 5,603,687 A | 2/1997 | Hori et al. | |
| 5,607,435 A | 3/1997 | Sachdeva et al. | |
| 5,621,574 A | 4/1997 | Foo | |
| 5,630,788 A | 5/1997 | Forkner et al. | |
| 5,647,368 A | 7/1997 | Zeng et al. | |
| 5,662,621 A | 9/1997 | Lafontaine | |
| 5,673,083 A | 9/1997 | Izumi et al. | |
| 5,685,311 A | 11/1997 | Hara | |
| 5,693,043 A | 12/1997 | Kittrell et al. | |
| 5,704,892 A | 1/1998 | Adair | |
| 5,716,323 A | 2/1998 | Lee | |
| 5,716,759 A | 2/1998 | Badehi | |
| 5,722,403 A | 3/1998 | McGee et al. | |
| 5,732,150 A | 3/1998 | Zhou et al. | |
| 5,740,808 A | 4/1998 | Panescu et al. | |
| 5,749,827 A | 5/1998 | Minami | |
| 5,751,340 A | 5/1998 | Strobl et al. | |
| 5,752,518 A | 5/1998 | McGee et al. | |
| 5,769,792 A | 6/1998 | Palcic et al. | |
| 5,772,597 A | 6/1998 | Goldberger et al. | |
| 5,776,049 A | 7/1998 | Takahashi | |
| 5,783,829 A | 7/1998 | Sealock et al. | |
| 5,784,098 A | 7/1998 | Shoji et al. | |
| 5,792,984 A | 8/1998 | Bloom | |
| 5,800,341 A | 9/1998 | McKenna et al. | |
| 5,807,261 A | 9/1998 | Benaron et al. | |
| 5,808,665 A | 9/1998 | Green | |
| 5,818,644 A | 10/1998 | Noda | |
| 5,827,172 A | 10/1998 | Takahashi et al. | |
| 5,827,531 A | 10/1998 | Morrison et al. | |

(56) References Cited

U.S. PATENT DOCUMENTS

| | | | |
|---|---|---|---|
| 5,840,017 A | 11/1998 | Furusawa et al. | |
| 5,846,185 A | 12/1998 | Carollo et al. | |
| 5,848,969 A | 12/1998 | Panescu et al. | |
| 5,865,729 A | 2/1999 | Meehan et al. | |
| 5,870,229 A | 2/1999 | Tsuchida | |
| 5,873,816 A | 2/1999 | Kagawa et al. | |
| 5,879,285 A | 3/1999 | Ishii | |
| 5,904,651 A | 5/1999 | Swanson et al. | |
| 5,908,445 A | 6/1999 | Whayne et al. | |
| 5,913,817 A | 6/1999 | Lee | |
| 5,916,155 A | 6/1999 | Levinson et al. | |
| 5,929,900 A | 7/1999 | Yamanaka et al. | |
| 5,940,126 A | 8/1999 | Kimura | |
| 5,947,894 A | 9/1999 | Chapman et al. | |
| 5,951,462 A | 9/1999 | Yamanaka | |
| 5,957,849 A | 9/1999 | Munro | |
| 5,971,915 A | 10/1999 | Yamamoto et al. | |
| 5,973,779 A | 10/1999 | Ansari et al. | |
| 5,980,663 A | 11/1999 | Badehi | |
| 5,989,185 A | 11/1999 | Miyazaki | |
| 5,998,878 A | 12/1999 | Johnson | |
| 5,999,327 A | 12/1999 | Nagaoka | |
| 6,008,123 A | 12/1999 | Kook et al. | |
| 6,014,919 A | 1/2000 | Jacobsen et al. | |
| 6,022,758 A | 2/2000 | Badehi | |
| 6,040,235 A | 3/2000 | Badehi | |
| 6,059,760 A * | 5/2000 | Sandmore et al. | 604/264 |
| 6,095,970 A | 8/2000 | Hidaka et al. | |
| 6,117,707 A | 9/2000 | Badehi | |
| 6,118,476 A | 9/2000 | Morito et al. | |
| 6,133,637 A | 10/2000 | Hikita et al. | |
| 6,134,003 A | 10/2000 | Tearney et al. | |
| 6,139,489 A | 10/2000 | Wampler et al. | |
| 6,139,819 A | 10/2000 | Unger et al. | |
| 6,142,930 A | 11/2000 | Ito et al. | |
| 6,161,035 A | 12/2000 | Furusawa | |
| 6,184,923 B1 | 2/2001 | Miyazaki | |
| 6,193,908 B1 | 2/2001 | Hampden-Smith et al. | |
| 6,211,955 B1 | 4/2001 | Basiji et al. | |
| 6,224,969 B1 | 5/2001 | Steenbergen et al. | |
| 6,261,226 B1 | 7/2001 | McKenna et al. | |
| 6,262,855 B1 | 7/2001 | Greisz | |
| 6,280,960 B1 | 8/2001 | Carr | |
| 6,288,172 B1 | 9/2001 | Goetz et al. | |
| 6,319,745 B1 | 11/2001 | Bertin et al. | |
| 6,322,498 B1 | 11/2001 | Gravenstein et al. | |
| 6,327,096 B1 | 12/2001 | Tsuchida | |
| 6,352,503 B1 | 3/2002 | Matsue | |
| 6,361,491 B1 | 3/2002 | Hasegawa et al. | |
| 6,366,726 B1 | 4/2002 | Wach et al. | |
| 6,375,635 B1 * | 4/2002 | Moutafis et al. | 604/43 |
| 6,384,397 B1 | 5/2002 | Takiar et al. | |
| 6,384,884 B1 | 5/2002 | Nakamura et al. | |
| 6,396,116 B1 | 5/2002 | Kelly et al. | |
| 6,407,768 B1 | 6/2002 | Ishikaw | |
| 6,445,939 B1 | 9/2002 | Swanson et al. | |
| 6,456,423 B1 | 9/2002 | Nayfeh et al. | |
| 6,471,636 B1 | 10/2002 | Sano et al. | |
| 6,485,413 B1 | 11/2002 | Boppart et al. | |
| 6,522,913 B2 | 2/2003 | Swanson et al. | |
| 6,525,866 B1 | 2/2003 | Lin et al. | |
| 6,533,722 B2 | 3/2003 | Nakashima | |
| 6,537,205 B1 | 3/2003 | Smith | |
| 6,551,302 B1 | 4/2003 | Rosinko et al. | |
| 6,552,796 B2 | 4/2003 | Magnin et al. | |
| 6,561,972 B2 | 5/2003 | Ooshima et al. | |
| 6,570,659 B2 | 5/2003 | Schmitt | |
| 6,573,950 B1 | 6/2003 | Hirata et al. | |
| 6,585,717 B1 | 7/2003 | Wittenberger et al. | |
| 6,595,913 B2 | 7/2003 | Takahashi | |
| 6,618,614 B1 | 9/2003 | Chance | |
| 6,622,367 B1 | 9/2003 | Bolduc et al. | |
| 6,643,071 B2 | 11/2003 | Schnitzer | |
| 6,658,279 B2 | 12/2003 | Swanson et al. | |
| 6,659,941 B2 | 12/2003 | Weber et al. | |
| 6,695,787 B2 | 2/2004 | Hogendijk et al. |
| 6,710,919 B1 | 3/2004 | Clausen |
| 6,719,686 B2 | 4/2004 | Coakley et al. |
| 6,727,313 B2 | 4/2004 | Zhou et al. |
| 6,756,437 B1 | 6/2004 | Xue et al. |
| 6,761,684 B1 | 7/2004 | Speier |
| 6,785,048 B2 | 8/2004 | Yamaguchi et al. |
| 6,826,422 B1 | 11/2004 | Modell et al. |
| 6,827,683 B2 | 12/2004 | Otawara |
| 6,833,916 B2 | 12/2004 | Osipchuk et al. |
| 6,834,158 B1 | 12/2004 | Templeton |
| 6,842,288 B1 | 1/2005 | Liu et al. |
| 6,850,659 B2 | 2/2005 | Han |
| 6,879,851 B2 | 4/2005 | McNamara et al. |
| 6,881,448 B1 | 4/2005 | Hattori |
| 6,891,984 B2 | 5/2005 | Petersen et al. |
| 6,893,432 B2 | 5/2005 | Intintoli et al. |
| 6,894,729 B2 | 5/2005 | Hirata et al. |
| 6,898,458 B2 | 5/2005 | Zeng et al. |
| 6,900,913 B2 | 5/2005 | Chen |
| 6,930,705 B2 | 8/2005 | Tanaka |
| 6,937,268 B2 | 8/2005 | Ogawa |
| 6,939,348 B2 | 9/2005 | Malecki et al. |
| 6,941,041 B2 | 9/2005 | Yamaguchi et al. |
| 6,944,204 B2 | 9/2005 | Zhou et al. |
| 6,953,432 B2 | 10/2005 | Schiefer |
| 6,956,624 B2 | 10/2005 | Hirata et al. |
| 6,960,165 B2 | 11/2005 | Ueno et al. |
| 6,982,740 B2 | 1/2006 | Adair et al. |
| 6,990,271 B2 | 1/2006 | Gafsi et al. |
| 7,030,904 B2 | 4/2006 | Adair et al. |
| 7,033,317 B2 | 4/2006 | Pruitt |
| 7,058,294 B2 | 6/2006 | Nakahara |
| 7,075,576 B2 | 7/2006 | Creasey et al. |
| 7,081,927 B2 | 7/2006 | Hirata et al. |
| 7,091,500 B2 | 8/2006 | Schnitzer |
| 7,098,871 B1 | 8/2006 | Tegreene et al. |
| 7,102,817 B1 | 9/2006 | Wu |
| 7,108,657 B2 | 9/2006 | Irion et al. |
| 7,153,299 B1 | 12/2006 | Tu et al. |
| 7,165,552 B2 | 1/2007 | Deem et al. |
| 7,166,537 B2 | 1/2007 | Jacobsen et al. |
| 7,167,317 B2 | 1/2007 | Jung et al. |
| 7,186,251 B2 | 3/2007 | Malecki et al. |
| 7,218,822 B2 | 5/2007 | Treado et al. |
| 7,221,388 B2 | 5/2007 | Sudo et al. |
| 7,234,816 B2 | 6/2007 | Bruzzone et al. |
| 7,247,847 B2 | 7/2007 | Webb et al. |
| 7,304,310 B1 | 12/2007 | Shortt et al. |
| 7,393,321 B2 | 7/2008 | Doguchi et al. |
| 7,420,675 B2 | 9/2008 | Giakos |
| 7,433,552 B2 | 10/2008 | Kiesel et al. |
| 7,511,891 B2 | 3/2009 | Messerschmidt |
| 7,554,597 B2 | 6/2009 | Scherling |
| 7,591,780 B2 | 9/2009 | Jacobsen |
| 7,629,659 B2 | 12/2009 | Jacobsen |
| 7,787,939 B2 | 8/2010 | Jacobsen et al. |
| 7,823,215 B2 | 10/2010 | Giakos |
| 7,835,074 B2 | 11/2010 | Jacobsen et al. |
| 7,842,046 B1 | 11/2010 | Nakao |
| 7,901,870 B1 | 3/2011 | Wach |
| 2001/0007051 A1 | 7/2001 | Nakashima |
| 2001/0007511 A1 | 7/2001 | Minami et al. |
| 2001/0012053 A1 | 8/2001 | Nakamura |
| 2001/0024848 A1 | 9/2001 | Nakamura |
| 2001/0049509 A1 | 12/2001 | Sekine et al. |
| 2002/0007110 A1 | 1/2002 | Irion |
| 2002/0034537 A1 | 3/2002 | Schulze et al. |
| 2002/0039594 A1 | 4/2002 | Unger |
| 2002/0080248 A1 | 6/2002 | Adair et al. |
| 2002/0109774 A1 | 8/2002 | Meron et al. |
| 2002/0111534 A1 | 8/2002 | Suzuki et al. |
| 2002/0166946 A1 | 11/2002 | Iizuka et al. |
| 2002/0166949 A1 | 11/2002 | Machida |
| 2002/0168776 A1 | 11/2002 | Cizdziel et al. |
| 2002/0188204 A1 | 12/2002 | McNamara |
| 2002/0193660 A1 | 12/2002 | Weber |
| 2003/0071342 A1 | 4/2003 | Honda et al. |
| 2003/0092995 A1 | 5/2003 | Thompson |

(56) References Cited

U.S. PATENT DOCUMENTS

| | | |
|---|---|---|
| 2003/0114732 A1 | 6/2003 | Webler et al. |
| 2003/0197812 A1 | 10/2003 | Hirata et al. |
| 2003/0199761 A1 | 10/2003 | Yock |
| 2003/0202127 A1 | 10/2003 | Hirata et al. |
| 2003/0208211 A1 | 11/2003 | Kortenbach |
| 2003/0220574 A1 | 11/2003 | Markus |
| 2003/0222325 A1 | 12/2003 | Jacobsen |
| 2004/0006274 A1 | 1/2004 | Giller et al. |
| 2004/0015049 A1 | 1/2004 | Zaar |
| 2004/0017961 A1 | 1/2004 | Petersen et al. |
| 2004/0059204 A1 | 3/2004 | Marshall |
| 2004/0097804 A1 | 5/2004 | Sobe |
| 2004/0111031 A1 | 6/2004 | Alfano et al. |
| 2004/0115955 A1 | 6/2004 | Motoyama et al. |
| 2004/0165858 A1 | 8/2004 | Curatolo |
| 2004/0181148 A1 | 9/2004 | Uchiyama et al. |
| 2004/0222031 A1 | 11/2004 | Szalony et al. |
| 2004/0225222 A1 | 11/2004 | Zeng et al. |
| 2004/0257566 A1 | 12/2004 | Chism |
| 2004/0260148 A1 | 12/2004 | Schnitzer |
| 2005/0054902 A1 | 3/2005 | Konno |
| 2005/0065504 A1 | 3/2005 | Melsky et al. |
| 2005/0084229 A1 | 4/2005 | Babbitt et al. |
| 2005/0088576 A1 | 4/2005 | Hirata et al. |
| 2005/0099824 A1 | 5/2005 | Dowling et al. |
| 2005/0124875 A1 | 6/2005 | Kawano et al. |
| 2005/0152421 A1 | 7/2005 | Fujitani |
| 2005/0154277 A1 | 7/2005 | Tang et al. |
| 2005/0158899 A1 | 7/2005 | Jacobsen et al. |
| 2005/0171521 A1 | 8/2005 | Brucker et al. |
| 2005/0174649 A1 | 8/2005 | Okada et al. |
| 2005/0187568 A1 | 8/2005 | Klenk et al. |
| 2005/0197534 A1 | 9/2005 | Barbato et al. |
| 2005/0226636 A1 | 10/2005 | Hiramatsu et al. |
| 2005/0231718 A1 | 10/2005 | Goodall et al. |
| 2005/0234345 A1 | 10/2005 | Yang |
| 2005/0264813 A1 | 12/2005 | Giakos |
| 2005/0267340 A1 | 12/2005 | Ishihara et al. |
| 2005/0288555 A1 | 12/2005 | Binmoeller |
| 2006/0009682 A1 | 1/2006 | Nagasawa et al. |
| 2006/0013593 A1 | 1/2006 | Yokoo et al. |
| 2006/0017928 A1 | 1/2006 | Crowther |
| 2006/0051036 A1 | 3/2006 | Treado |
| 2006/0069312 A1 | 3/2006 | O'Connor |
| 2006/0079835 A1 | 4/2006 | Frassica |
| 2006/0106283 A1 | 5/2006 | Wallace et al. |
| 2006/0135921 A1 | 6/2006 | Wiercinski et al. |
| 2006/0142700 A1 | 6/2006 | Sobelman et al. |
| 2006/0146172 A1 | 7/2006 | Jacobsen et al. |
| 2006/0161048 A1 | 7/2006 | Squicciarini |
| 2006/0181774 A1 | 8/2006 | Ojima et al. |
| 2006/0252994 A1 | 11/2006 | Ratnakar |
| 2006/0253088 A1 | 11/2006 | Chow et al. |
| 2007/0010709 A1 | 1/2007 | Reinschke |
| 2007/0032796 A1 | 2/2007 | Chin-Chen et al. |
| 2007/0066869 A1 | 3/2007 | Hoffman |
| 2007/0073321 A1 | 3/2007 | Mikkaichi et al. |
| 2007/0083232 A1 | 4/2007 | Lee |
| 2007/0088276 A1 | 4/2007 | Stubbs et al. |
| 2007/0135803 A1 | 6/2007 | Belson |
| 2007/0146887 A1 | 6/2007 | Ikeda et al. |
| 2007/0208252 A1 | 9/2007 | Makower |
| 2007/0228300 A1 | 10/2007 | Smith |
| 2007/0233187 A1 | 10/2007 | Lobello |
| 2007/0239066 A1 | 10/2007 | Laham et al. |
| 2007/0255392 A1 | 11/2007 | Johnson |
| 2007/0293727 A1 | 12/2007 | Goldfarb et al. |
| 2008/0045794 A1 | 2/2008 | Belson |
| 2008/0058601 A1 | 3/2008 | Fujimori |
| 2008/0071141 A1 | 3/2008 | Gattani et al. |
| 2008/0094326 A1 | 4/2008 | Yamaki et al. |
| 2008/0114309 A1 | 5/2008 | Zuckerman |
| 2008/0143822 A1 | 6/2008 | Wang et al. |
| 2008/0160257 A1 | 7/2008 | Takada et al. |
| 2008/0177141 A1 | 7/2008 | Wu et al. |
| 2008/0183080 A1 | 7/2008 | Abraham |
| 2008/0188767 A1 | 8/2008 | Oaki et al. |
| 2008/0227893 A1 | 9/2008 | Tamori et al. |
| 2008/0267562 A1 | 10/2008 | Wang et al. |
| 2009/0027765 A1 | 1/2009 | Kamijima |
| 2009/0036764 A1 | 2/2009 | Rivas et al. |
| 2009/0054791 A1 | 2/2009 | Flusberg |
| 2009/0082626 A1 | 3/2009 | Ichimura et al. |
| 2009/0119808 A1 | 5/2009 | Giakos |
| 2009/0137928 A1 | 5/2009 | Quick et al. |
| 2009/0143645 A1 | 6/2009 | Matthes |
| 2009/0155371 A1 | 6/2009 | Sojka et al. |
| 2009/0156899 A1 | 6/2009 | Konishi |
| 2009/0180197 A1 | 7/2009 | Jacobsen et al. |
| 2009/0213894 A1 | 8/2009 | Grapov et al. |
| 2009/0234325 A1 | 9/2009 | Rozenberg et al. |
| 2009/0267270 A1 | 10/2009 | Murakami et al. |
| 2009/0287048 A1 | 11/2009 | Jacobson et al. |
| 2009/0306474 A1 | 12/2009 | Wilson |
| 2010/0016662 A1 | 1/2010 | Salsman et al. |
| 2010/0085567 A1 | 4/2010 | Dottery et al. |
| 2010/0106134 A1 | 4/2010 | Jolly et al. |
| 2010/0134872 A1 | 6/2010 | Johnson et al. |
| 2010/0171821 A1 | 7/2010 | Jacobsen et al. |
| 2010/0248178 A1 | 9/2010 | Nahlieli |
| 2011/0204265 A1 | 8/2011 | Smith et al. |

FOREIGN PATENT DOCUMENTS

| | | |
|---|---|---|
| DE | 19859434 | 7/2000 |
| EP | 0482797 | 4/1992 |
| EP | 0550 995 | 7/1993 |
| EP | 0639043 | 2/1995 |
| EP | 0681809 | 11/1995 |
| EP | 1104182 | 5/2001 |
| EP | 1195130 | 4/2002 |
| EP | 1477104 | 11/2004 |
| EP | 1488737 | 12/2004 |
| EP | 1626436 | 2/2006 |
| EP | 1647569 | 4/2006 |
| EP | 1880656 | 1/2008 |
| JP | 58-046924 | 3/1983 |
| JP | 63-155115 | 6/1988 |
| JP | H05-039501 | 2/1993 |
| JP | 5-049602 | 3/1993 |
| JP | H07-148105 | 6/1995 |
| JP | H07-222712 | 8/1995 |
| JP | 08-076028 | 3/1996 |
| JP | 08084700 | 4/1996 |
| JP | H09-021963 | 1/1997 |
| JP | 11 137512 | 5/1999 |
| JP | 2001/314365 | 11/2001 |
| JP | 2004-086553 | 3/2004 |
| JP | 2004/329700 | 11/2004 |
| JP | 2005334462 | 8/2005 |
| JP | 2006/162418 | 6/2006 |
| JP | 2006/320369 | 11/2006 |
| JP | 2007-167387 | 7/2007 |
| JP | 2007/312290 | 11/2007 |
| JP | 2009/067946 | 4/2009 |
| KR | 10-2008002793 | 3/2008 |
| WO | WO98/38907 | 9/1998 |
| WO | WO99/40624 | 8/1999 |
| WO | WO00/54033 | 9/2000 |
| WO | WO 03/008183 | 10/2003 |
| WO | WO 03/081831 | 10/2003 |
| WO | WO2006/060777 | 6/2006 |
| WO | WO 2007/138889 | 12/2007 |

OTHER PUBLICATIONS

Boppart, S.A. et al., "Optical imaging technology in minimally invasive surgery," Surg. Endosc., 1999, vol. 13, pp. 718-722.

Fujimoto, JG et al., "High resolution in vivo intra-arterial imaging with optical coherence tomography," Heart, 1999, vol. 82, pp. 128-133.

Hirofumi Tsuchida et al., "Design of imaging lens systems that use low dispersive radial gradient-index rod," Jpn, J. Appl. Phys. vol. 37 No. 6B, Jun. 30, 1998, pp. 3633-3637.

(56) References Cited

OTHER PUBLICATIONS http://news.thomasnet.com/fullstory/23462, "Near-IR Camera Utilizes CCD Array with Phosphor Coating"; Jun. 11, 2003; 5 pages.
J. Knittel et al., "Endoscope-compatible confocal microscope using a gradient index-lens system" Optics Communications, vol. 188, Issue 5-6, Feb. 2001, pp. 267-273.
Jacobsen, Stephen C., U.S. Appl. No. 10/391,489, filed Mar. 17, 2003.
Jacobsen, Stephen C., U.S. Appl. No. 10/391,490, filed Mar. 17, 2003.
Jacobsen, Stephen C., U.S. Appl. No. 10/391,513, filed Mar. 17, 2003.
Jacobsen, Stephen C., U.S. Appl. No. 11/292,902, filed Dec. 1, 2005.
Jacobsen, Stephen C., U.S. Appl. No. 11/810,702, filed Jun. 5, 2007.
Jacobsen, Stephen C., U.S. Appl. No. 12/008,486, filed Jan. 11, 2008.
Jacobsen, Stephen C., U.S. Appl. No. 12/079,741, filed Mar. 27, 2008.
Jacobsen, Stephen C., U.S. Appl. No. 12/152,730, filed May 16, 2008.
Jacobsen, Stephen C., U.S. Appl. No. 12/487,481, filed Jun. 18, 2009.
Jacobsen, Stephen C., U.S. Appl. No. 12/487,495, filed Jun. 18, 2009.
Jacobsen, Stephen C., U.S. Appl. No. 12/512,188, filed Jul. 30, 2009.
Jacobsen, Stephen C.; U.S. Appl. No. 12/611,776, filed Nov. 3, 2009.
Jacobsen, Stephen C.; U.S. Appl. No. 12/792,562, filed Jun. 2, 2010.
Jacobsen, Stephen C.; U.S. Appl. No. 12/896,731, filed Oct. 1, 2010.
Jacobsen, Stephen C.; U.S. Appl. No. 12/896,732, filed Oct. 1, 2010.
Jacobsen, Stephen C.; U.S. Appl. No. 12/896,737, filed Oct. 1, 2010.
Jacobsen, Stephen C.; U.S. Appl. No. 12/896,743, filed Oct. 1, 2010.
Jacobsen, Stephen C.; U.S. Appl. No. 12/938,672, filed Nov. 3, 2010.
Jacobsen, Stephen C.; U.S. Appl. No. 12/946,442, filed Nov. 15, 2010.
Johansson et al.; "Generation of Turquoise Light by Sum Frequency Mixing of a Diode-Pumped Solid-State Laser and a Laser Diode in Periodically Poled KTP," Optics Express; Oct. 4, 2004; pp. 4935-4940; vol. 12, No. 12.
Literature from GRIN TECH, "In vivo medical confocal imaging and optical coherence tomography," www.grintech.de, Revision Jun. 2001, pp. 1-3.
Microcam, Minast Project 5.04, Nov. 11, 1999, http://www.imt.unine.ch/ESPLAB/www/projects/Microcam/, pp. 1-16.
Nguyen, Clark, "Communications Applications of Microelectromechanical Systems," Proceedings, Sensors Expo, May 19-21, 1998, San Jose, CA. pp. 447-455.
Tearney, G.J. et al., "Scanning single-mode fiber optic catheter-endoscope for optical coherence tomography," Optics Letters, Apr. 1, 1996, vol. 21, No. 7, pp. 543-545.
Zeis, Michael et al., "Color Business Report," ISSN 1055-3339. Jul. 2002, p. 5.
Gaoping et al.; Research on the Measurement of Grin Lens Focused Spot Diameter and Resolution; Applied Optics; 1995; vol. 16, No. 6.
PCT Application PCT/US2010/051200; filed Oct. 1, 2010; Stephen C. Jacobsen; ISR mailed Jun. 3, 2011.
PCT Application PCT/US2010/051198; filed Oct. 1, 2010; Stephen C. Jacobsen; ISR mailed Jun. 3, 2011.
PCT Application PCT/US2010/051192; filed Oct. 1, 2010; Stephen C. Jacobsen; ISR mailed May 30, 2011.
PCT Application PCT/US2010/051188; filed Oct. 1, 2010; Stephen C. Jacobsen; International Search Report mailed Jul. 13, 2011.
Xie et al; GRIN Lens Rod Based Probe for Endoscopic Spectral Domain Optical Coherence Tomography with Fast Dynamic Focus Tracking; Optics Express; Apr. 17, 2006; 9 pp.; vol. 14, No. 8.
Xuting Technologies Co., Ltd.; http://www.xutingby.com/en/products/glinfo.htm; as accessed May 1, 2008; 5 pages.
Frequency; Wikipedia, The Free Encyclopedia; http://en.wikipedia.org/wiki/Frequency; as accessed May 9, 2008; 4 pages.
Introduction to Gradient Index Optics; http://grintech.de/e_main_grin.htm; as accessed May 1, 2008; 7 pages.
Gradient Index (GRIN) Lenses; Grin Tech; 2 pages; The Applicant believes the year of publication of this article is prior to the effective US filing date of this patent application.
Shape Memory Polymers—Biodegradable Sutures; http://www.azom.com/details.asp?ArticleID=1542; as accessed Nov. 6, 2007; 4 pages.
Surgical Needles for Use With Sutures; Wikipedia, The Free Encyclopedia; as accessed Nov. 6, 2007; 6 pages.
Harder et al; Against the Migraine; Science News Online; http://www.sciencenews.org/articles/20050219/bob8.asp; Feb. 19, 2005; 11 pages.
U.S. Appl. No. 12/152,730, filed May 16, 2008; Stephen C. Jacobson; office action issued Sep. 16, 2011.
U.S. Appl. No. 12/487,481, filed Jun. 18, 2009; Stephen C. Jacobsen; office action dated Oct. 12, 2012.
U.S. Appl. No. 12/512,188, filed Jul. 30, 2009; Stephen C. Jacobsen; office action dated Nov. 19, 2012.
Obreja et al.; "Poly (vinyl-alcohol) Films for Microphotonics"; 2004, IEEE, pp. 1-4.
Subrahmanyam et al; Lens Aberrations; A Text Book of Optics; Jan. 1, 2004; Chapter 9, pp. 199-200; ; S. Chand & Co. Ltd.
Office Action for U.S. Appl. No. 13/940,791 dated May 8, 2015, 28 pages.
Office Action for U.S. Appl. No. 13/966,030 dated Aug. 6, 2015, 28 pages.

\* cited by examiner

METHOD AND APPARATUS FOR MANIPULATING MOVEMENT OF A MICRO-CATHETER

CLAIM OF PRIORITY

This application claims priority to U.S. Provisional Application 61/247,886 filed on Oct. 1, 2009 which is incorporated herein by reference in its entirety.

FIELD OF THE INVENTION

The present invention relates to medical devices, and more particularly to miniaturized in-situ imaging devices and methods of operation of said devices.

BACKGROUND

Catheters have been in use for medical procedures for many years to examine, diagnose, and treat patients. The movement of a catheter through the vasculature of a patient to probe deeply for a considerable depth or through branching vessels requires that the tip of the catheter be steerable (e.g., bendable or deflectable to travel at an angle when a secondary branch of the vasculature is reached).

One presently known form of a catheter having a steerable tip at the distal end comprises a plurality of control wires running from the steerable tip to the proximal end at which steering means are provided for operating the control wires to bend the steerable tip.

SUMMARY OF THE INVENTION

It has been recognized that it would be advantageous to develop a steerable micro-catheter capable of navigating portions of a patient without the use of control wires or microactuators within the micro-catheter.

In one exemplary embodiment, the invention provides a medical device comprising an elongated tubular member having at least one lumen therein. The lumen is proximally coupled to a pressurized fluid control system configured to regulate fluid flow through the elongated tubular member. An aperture is disposed near a distal end of the elongated tubular member, the aperture being in fluid communication with the at least one lumen. In one aspect, the aperture is oriented at an angle which is non parallel to the longitudinal axis of the elongated tubular member. A nozzle is coupled to the aperture, wherein the nozzle is configured to regulate pressurized flow out of the catheter to manipulate movement of the distal end of the elongated tubular member.

In an additional exemplary embodiment, the invention provides a method of manipulating movement of a micro-catheter within a patient comprising advancing a portion of a micro-catheter into a patient, the micro-catheter having at least one aperture in fluid communication with a lumen of the micro-catheter. The aperture is disposed near a distal end of the micro-catheter and is oriented non-parallel to the longitudinal axis of the micro-catheter. The method further comprises bending a distal portion of the micro-catheter by creating at least one fluid-flow-induced moment force on a distal end of the micro-catheter, wherein the at least one fluid-flow-induced moment force is created by injecting a pressure-regulated fluid through the micro-catheter and out of the at least one aperture.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention they are, therefore, not to be considered limiting of its scope. It will be readily appreciated that the components of the present invention, as generally described and illustrated in the figures herein, could be arranged and designed in a wide variety of different configurations. Nonetheless, the invention will be described and explained with additional specificity and detail through the use of the accompanying drawings in which:

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

It must be noted that, as used in this specification and the appended claims, singular forms of "a," "an," and "the" include plural referents unless the context clearly dictates otherwise.

An "SSID," "solid state imaging device," "SSID chip," or "solid state imaging chip" in the exemplary embodiments generally comprises an imaging array or pixel array for gathering image data. In one embodiment, the SSID can comprise a silicon or other semiconductor substrate or amorphous silicon thin film transistors (TFT) having features typically manufactured therein. Features can include the imaging array, conductive pads, metal traces, circuitry, etc. Other integrated circuit components can also be present for desired applications. However, it is not required that all of these components be present, as long as there is a means of gathering visual or photon data, and a means of sending that data to provide a visual image or image reconstruction.

The term "umbilical" can include the collection of utilities that operate the SSID or the micro-camera as a whole. Typically, an umbilical includes a conductive line, such as electrical wire(s) or other conductors, for providing power, ground, clock signal, and output signal with respect to the SSID, though not all of these are strictly required. For example, ground can be provided by another means than through an electrical wire, e.g., to a camera housing such as micromachined tubing, etc. The umbilical can also include other utilities such as a light source, temperature sensors, force sensors, fluid irrigation or aspiration members, pressure sensors, fiber optics, microforceps, material retrieval tools, drug delivery devices, radiation emitting devices, laser diodes, electric cauterizers, and electric stimulators, for example. Other utilities will also be apparent to those skilled in the art and are thus comprehended by this disclosure.

"GRIN lens" or "graduated refractive index lens" refers to a specialized lens that has a refractive index that is varied radially from a center optical axis to the outer diameter of the lens. In one embodiment, such a lens can be configured in a cylindrical shape, with the optical axis extending from a first flat end to a second flat end. Thus, because of the differing refractive index in a radial direction from the optical axis, a lens of this shape can simulate the affects of a more traditionally shaped lens. Exemplary GRIN lenses may include, but are not limited to, a GRIN rod lens. However, any suitable GRIN lens may be used herein.

With these definitions in mind, reference will now be made to the accompanying drawings, which illustrate, by way of example, embodiments of the invention.

Manipulation of movement of medical devices within portions of a patient can be particularly useful in medical diagnostic and treatment applications. For example, portions of human anatomy previously viewable only by a surgical procedure can be viewed now by minimally invasive procedures, provided an imaging device can be made that is small enough to view the target anatomy. Advantageously, manipulation of the movement of the imaging device without the need for special wires or heating elements within the imaging device provides a safer, more efficient means of advancing the medical device within tortuous portions of the anatomy of the patient. While the present invention has applications in these aforementioned fields and others, the medical imaging application can be used to favorably illustrate unique advantages of the invention.

Figure 1:
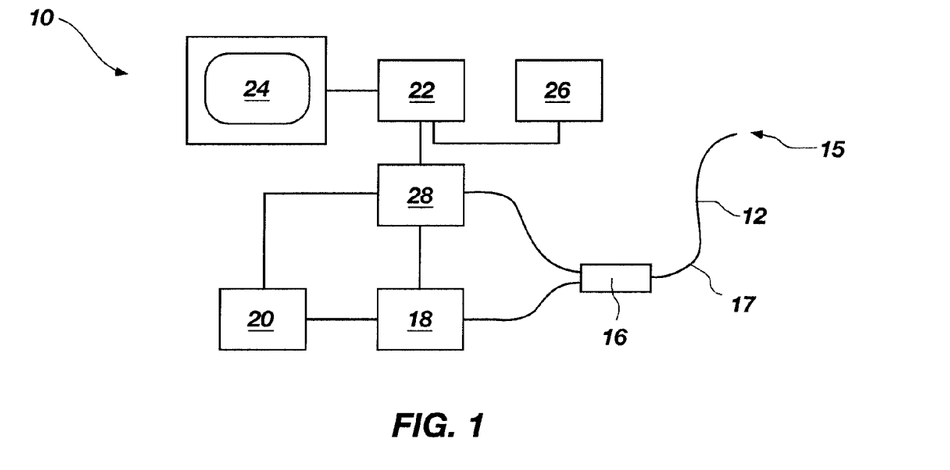
FIG. 1 is a medical device in accordance with an embodiment of the present invention.
Figure 2:
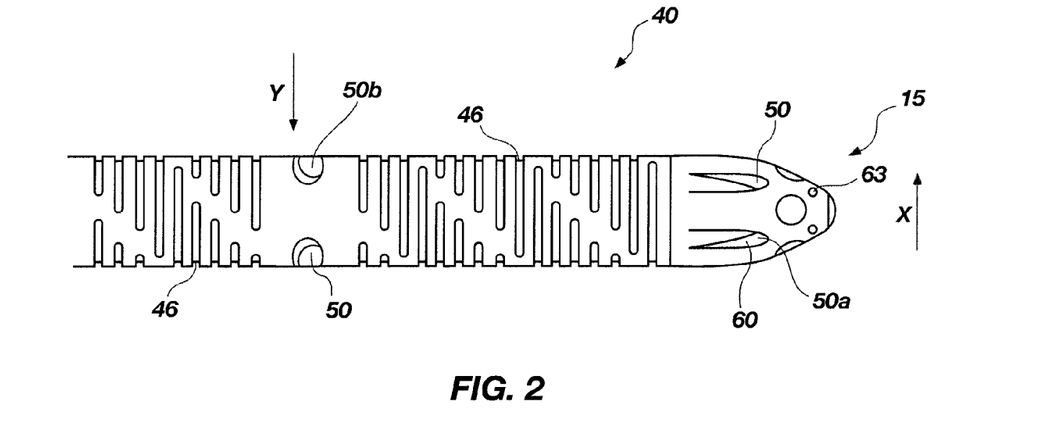
FIG. 2 is a side view of a distal end of a micro-catheter in accordance with one embodiment of the present invention.

With reference to FIG. 1, in one embodiment of the invention, a medical imaging and fluid pressure control system 10 comprises a micro-catheter 12 having an imaging device disposed at a distal tip 15 of the micro-catheter 12. A processor 22, such as an appropriately programmed computer, is provided to control the imaging system 10 and create an image of anatomy adjacent the distal tip portion 15, within a patient (not shown), displayable on a monitor 24, and storable in a data storage device 26. An interface 28 is provided which supplies power to the imaging device and feeds a digital image signal to the processor based on a signal received from the imaging device via an electrical umbilical, including conductive wires through the micro-catheter 12. In one aspect, the system further includes a fitting 16 enabling a fluid, such as a clear saline solution, to be jetted out of the distal tip portion of the micro-catheter 12 from a reservoir 18 through the micro-catheter to manipulate movement of the micro-catheter. A pump 20 is provided, and is manually actuated by a medical practitioner performing a medical imaging procedure, or can be automated and electronically controlled so as to dispense fluid on demand according to control signals from the practitioner, sensors, or according to software commands.

With reference generally to FIGS. 1-6, in one embodiment of the present invention, the distal end 15 of a medical device is shown comprising micro-catheter 12 having at least one lumen 45 therein. The lumen 45 is proximally coupled to a pressurized fluid control system 10 configured to regulate fluid flow through the micro-catheter 12. An aperture 50 is disposed near a distal end 15 of the micro-catheter 12 in fluid communication with the at least one lumen 45. In one aspect of the invention, the aperture 50 is oriented at an angle which is non parallel to the longitudinal axis of the elongated tubular member 40. The medical device further comprises a nozzle 55 coupled to the aperture 50, wherein the nozzle 55 is configured to regulate pressurized flow out of the micro-catheter 12 to manipulate movement of the distal end 15 of the micro-catheter 40. In one aspect of the invention, the aperture 50 and nozzle 55 are disposed within a recess 60 of the micro-catheter 12. Advantageously, by jetting fluid through any nozzle 55, a fluid-flow-induced moment force is created directing the distal end 15 of micro-catheter 12 in a direction opposite the direction of the fluid jet.

In another embodiment of the present invention, the micro-catheter 12 further comprises a plurality of apertures 50 having a nozzle 55 disposed therein near a distal end 15 of the micro-catheter 12. The plurality of apertures 50 are in fluid communication with the at least one lumen 45. In another aspect, the micro-catheter 12 comprises a plurality of lumens wherein each lumen is in fluid communication with the plurality of apertures 50.

The apertures 50 and nozzles 55 are oriented such that fluid jetted from the nozzle 55 creates a fluid-flow-induced moment force directing portions of the micro-catheter 12 in a direction opposite the direction of fluid flow. Advantageously, by jetting a fluid from nozzles 55a and 55b, for example, a user may create a bending moment force acting on micro-catheter 12 by creating a fluid-flow-induced moment force in direction X at the distal end 15 of micro-catheter 12 and a complementary fluid-flow-induce force in direction Y at a longitudinal distance away from the distal end 15 of micro-catheter 12. It is understood and contemplated herein that numerous apertures and nozzles can be placed along numerous locations of the micro-catheter 12 as suits a particular application. For example, aperture 50a (and associated nozzle) may be disposed on a distal end of micro-catheter 12 with aperture 50b disposed on micro-catheter a predetermined distance along the longitudinal axis of micro-catheter 12. In like manner, other apertures (not shown) may be placed further down the longitudinal axis of the micro-catheter 12 as suits a particular application. Further, the apertures (and associated nozzles) may be positioned at different locations about the circumference of the micro-catheter 12 (e.g., linearly or in a helix configuration, etc.) as suits a particular application. These apertures (and associated nozzles) may be configured and oriented (i.e., the angle of the aperture with respect to the outer surface of micro-catheter 12) to assist in steering or propelling the micro-catheter 12 as desired.

The micro-catheter 12 can be configured to be bendable and flexible so as to be steerable within a patient's anatomy and to minimize trauma. For example, the micro-catheter 12 can comprise a micromachined portion 46 at the distal tip portion 15, and cut-out portions (not shown) which allow for increased flexibility of the tube. Such a micromachined tube can also allow bending to facilitate guiding the micro-catheter to a desired location by selection of desired pathways as the micro-catheter is advanced. Additional details on construction of similar slotted micro-machined tube or segments can be found in U.S. Pat. No. 6,428,489, which is incorporated herein by reference. In one aspect, the micro-catheter has a maximum diameter of less than about 760 micrometers. In another aspect, the micro-catheter 12 has a stiffening member (not shown) removably inserted into the at least one lumen 45.

Figure 3:
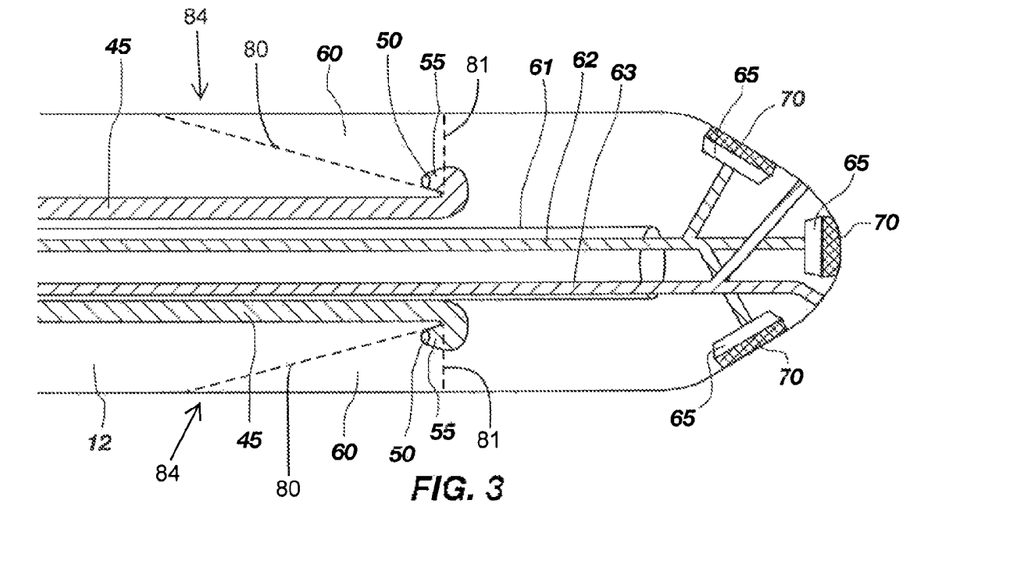
FIG. 3 is cross-sectional view of the micro-catheter of FIG. 2.
Figure 4:
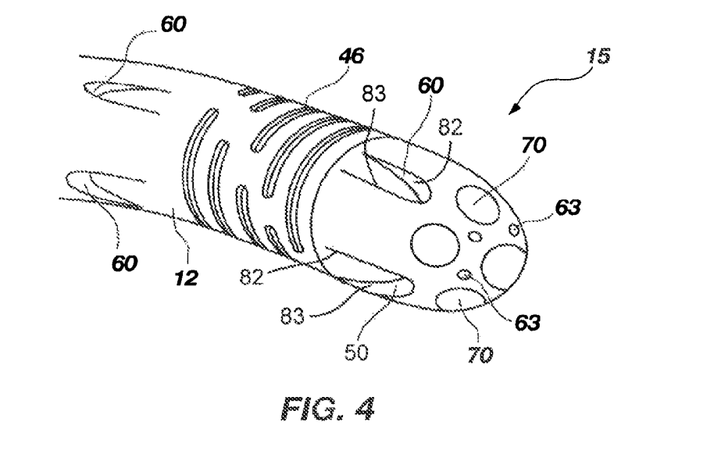
FIG. 4 is a perspective view of a micro-catheter in accordance with one embodiment of the present invention.
Figure 5:
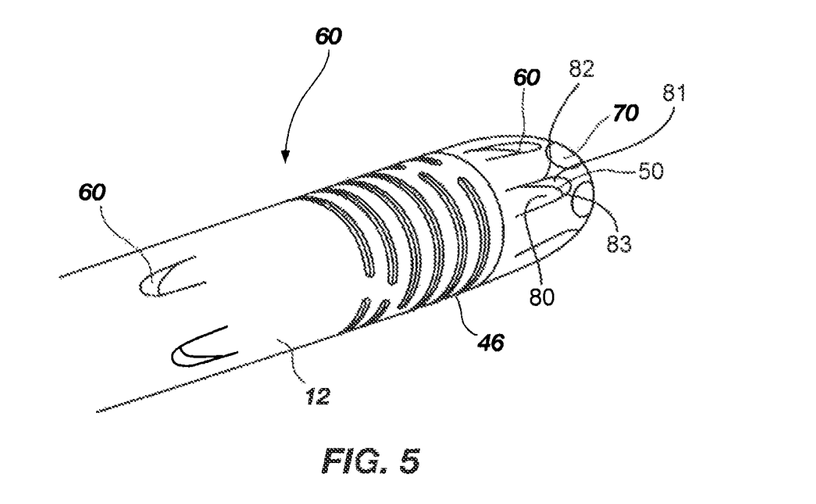
FIG. 5 is an additional perspective view of the micro-catheter of FIG. 4.
Figure 6:
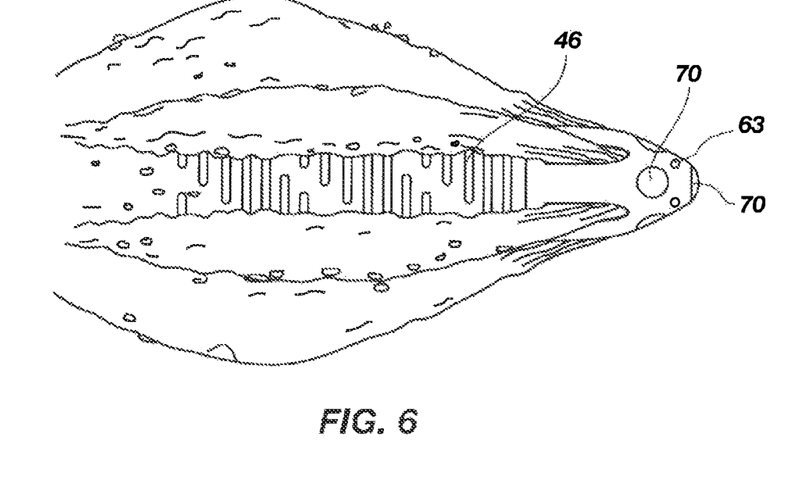
FIG. 6 is a side view of the micro-catheter of FIG. 4 illustrating jetting of a fluid from apertures of the micro-catheter.

With more specific reference to FIG. 3, the micro-catheter 12 can include an umbilical 61, which can include electrical wires 62 and/or a light source 63, for example. Other components that can be included within the micro-catheter 12 can include, temperature sensors, force sensors, fluid irrigation or aspiration members, pressure sensors, microforceps, material retrieval tools, drug delivery devices, radiation emitting devices, laser diodes, electric cauterizers, and electric stimulators.

In one aspect, the micro-catheter 12 can also comprise an SSID or solid state imaging device 65 that includes an imaging array (not shown) and conductive pads for coupling the electrical wires 62 to the SSID 65. The light source shown is a fiber optic. However, other light sources can be used, such as those carried by the SSID 65. For example, the SSID 65 can also include light-emitting diodes (LEDs) configured to illuminate the area immediately adjacent the distal tip portion 15. With the SSID 65 in this configuration, a GRIN lens 70 is shown optically coupled to the imaging array of the SSID 65. In one embodiment of the present invention, the SSID 65 has a maximum width of approximately 450 microns.

The GRIN lens 70 can be substantially cylindrical in shape. In one embodiment, the GRIN lens 70 can have a first flat end for receiving light, a second flat end for passing the light to the imaging array, and an outer curved surface surrounded by an opaque coating or sleeve member to prevent unwanted light from entering the GRIN lens 70. The GRIN lens 70 can be optically coupled to the imaging array by direct contact between the second flat end and the imaging array of the SSID 65. Such direct contact can include an optically transparent or translucent bonding material at the interface between the second flat end and the imaging array. Alternatively, the GRIN lens 70 can be optically coupled to the imaging array of the SSID 65 through an intermediate optical device, such as a fiber optic or a color filter, or any shape optical lens such as a prism or wide angle lens. As will also be appreciated, while the system is illustrated by the exemplary embodiment of a medical imaging system, these arrangements could be used in other devices, such as visual sensors in other devices, surveillance apparatus, and in other applications where a very small imaging device can be useful.

Moreover, with reference to all of the embodiments described herein, the device contemplated can be very small in size, and accordingly, the imaging array of the SSID can have a lower pixel count than would otherwise be desirable. As technology advances, pixel size can be reduced, thereby providing clearer images and data. However, when using a lower number of pixels in an imaging array, the resolution of the image provided by the device can be enhanced through software in processing image data received from the SSID.

The processor showing in FIG. 1, can be appropriately programmed to further resolve a scanned image from an array of an SSID, for example, based on information received as the SSID is moved slightly, such as from controlled vibration. The processor can analyze how such image data from the imaging array is altered due to the vibration, and can refine the image based on this information.

Figure 7:
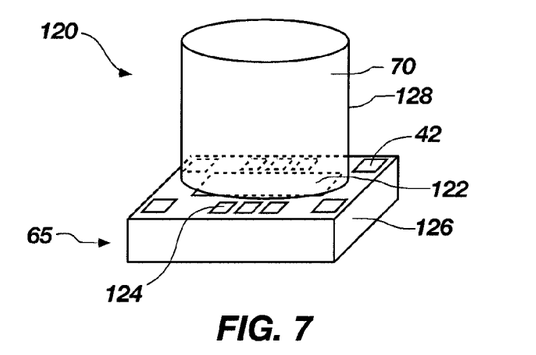
FIG. 7 is a perspective view of an SSID optically coupled to a GRIN lens in accordance with one embodiment of the present invention.

Referring now to FIG. 7, a system, indicated generally at 120, includes a GRIN lens 70 and an SSID 65. The SSID 65 can comprise a silicon or other semiconductor substrate or amorphous silicon thin film transistors (TFT) 126 having features typically manufactured therein. Features including the imaging array 122, the conductive pads 42, metal traces (not shown), circuitry (not shown), etc., can be fabricated therein. With respect to the conductive pads, the connection between conductive pads and a conductive line of an umbilical (not shown) can be through soldering, wire bonding, solder bumping, eutectic bonding, electroplating, and conductive epoxy. However, a direct solder joint having no wire bonding between the electrical umbilical and the conductive pads is also contemplated herein. In one embodiment, the conductive line of the umbilical provides power, ground, clock signal, and output signal with respect to the SSID 65. Other integrated circuit components can also be present for desired applications, such as light emitting diodes (LEDs) 124, for providing light to areas around the GRIN lens 70.

It is not required that all of these components be present, as long as there is a visual data gathering and sending image device present, and some means provided to connect the data gathering and sending device to a visual data signal processor. Other components, such as the umbilical, housing, adaptors, utility guides, and the like, can also be present, though they are not shown in FIG. 7. The SSID 65 can be any solid state imaging device, such as a CCD, a CID, or a CMOS imaging device. Also shown, the GRIN lens 70 is coated with an opaque coating 128 on the curved surface to prevent light from entering the lens at other than the flat surface that is most distal with respect to the SSID 65.

Figure 8:
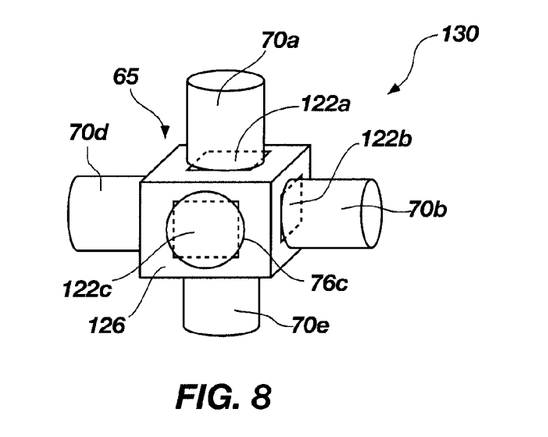
FIG. 8 is a perspective view of an exemplary embodiment of an SSID and multiple GRIN lens positioned in an array.

With reference to FIG. 8, one embodiment of an imaging system 130 is depicted that includes multiple imaging arrays 122*a*, 122*b*, 122*c* on a common SSID 65. Though only three imaging arrays are shown in this perspective view, five imaging arrays are present in this embodiment (i.e., one on each side of five sides of the substrate 126, with the back side of the substrate providing a surface for umbilical connection). Each imaging array is respectively optically coupled to a GRIN lens 70*a*, 70*b*, 70*c*, 70*d*, 70*e*. As can be appreciated, this is but one configuration where multiple imaging arrays with multiple GRIN lenses can be used. Fewer or more imaging arrays can be used in other similar embodiments, and/or can be part of multiple SSIDs. Umbilical connections are not shown, though it is understood that an umbilical can be present to operate the SSID 65 and its multiple imaging arrays (either by signal splitting or by the use of separate power and/or signal sources).

Figure 9:
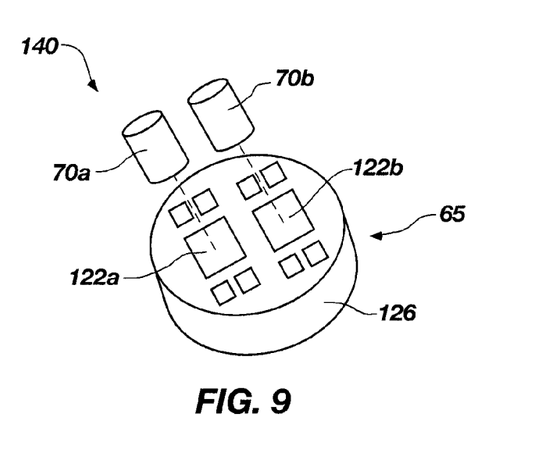
FIG. 9 is a perspective view of another exemplary embodiment of an SSID and multiple GRIN lens positioned in an array.

FIG. 9 depicts a system, shown generally at 140, which can provide stereoscopic imaging. Specifically, multiple imaging arrays 122*a*, 122*b*, are shown on a common SSID 65 in a coplanar arrangement. A pair of GRIN lenses 70*a*, 70*b* are shown as they would be optically coupled to imaging arrays 122*a*, 122*b*, respectively. Other than the imaging array, other features are also present in the SSID 65, including conductive pads 42 for providing an electrical connection to an umbilical (not shown). Additional principles of operation and details of construction of similar imaging assemblies can be found in U.S. patent application Ser. Nos. 10/391,489, 10/391,490, 11/292,902, and 10/391,513 each of which are incorporated herein by reference in their entireties.

With reference to FIGS. 1-6, in an additional embodiment of the present invention, a method of manipulating movement of a micro-catheter 12 within a patient is disclosed. The method comprises advancing a portion of a micro-catheter 12 into a patient, the micro-catheter 12 having at least one aperture 50 in fluid communication with a lumen 45 of the micro-catheter 12. The aperture 50 is disposed near a distal end 15 of the micro-catheter 12 and is oriented non parallel to the longitudinal axis of the micro-catheter 12. The method further comprises bending a distal portion 15 of the micro-catheter 12 by creating at least one fluid-flow-induced moment force on a distal end 15 of the micro-catheter 12, wherein the at least one fluid-flow-induced moment force is created by injecting a pressure-regulated fluid through the micro-catheter 12 and out of the at least one aperture 50.

In another embodiment of the invention, the micro-catheter 12 further comprises at least one SSID 65 disposed on a distal end 15 of the micro-catheter 12 and at least one GRIN lens 70 disposed on a distal end of the SSID 65. The SSID 65 and GRIN lens 70 are used in connection with an image processing and viewing assembly 10 for viewing an internal portion of the patient while advancing the micro-catheter 12 within the patient. The micro-catheter 12 further comprises a flexible distal segment 15 and a semi-rigid proximal segment 17. The micro-catheter 12 has a plurality of lumens 45 and a plurality of apertures 50 in fluid communication with the plurality of lumens 45. The plurality of apertures 50 are each oriented non parallel to the longitudinal axis of the micro-catheter 12. The plurality of lumens 45 are configured to selectively convey pressure-regulated fluids through the apertures 50 based on demand according to control signals from the user, sensors, or according to software commands.

In one embodiment, the method further comprises creating a second fluid-flow induced moment force by injecting fluid through a second aperture 50b. The direction of the second fluid-flow-induced moment force is oriented non parallel to the first fluid-flow-induced moment force which is created from jetting fluid through a first aperture 50a. In another aspect of the invention, the method comprises creating a second fluid-flow-induced moment force by injecting fluid through a second aperture 50b, the second aperture being disposed about parallel to the first aperture 50a and longitudinally spaced from the first aperture 50a. In yet another aspect, the direction of the second fluid-flow-induced moment force is about opposite the direction of the first fluid-flow-induced moment force. In still another aspect of the invention, the first fluid-flow-induced moment force is greater than the second fluid-flow-induced moment force.

In accordance with one aspect of the invention, a recess 60 is disposed about the micro-catheter 12 and near a distal end of the micro-catheter 12, the recess 60 has a bottom wall 80 that is non-parallel to a longitudinal axis of the micro-catheter 12, a back wall 81 disposed at a distal end of the recess 60, and a pair of opposing sidewalls 82, 83 extending from a front 84 of the recess 60 to the back wall 81 that enclose an aperture 50 therein. The aperture 50 is disposed near a distal end of the micro-catheter 12 in fluid communication with a lumen 45.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A method of manipulating movement of a device within a patient comprising:
   advancing an elongate tubular member into the patient, the elongate tubular member comprising:
   (i) at least one lumen therein, wherein the at least one lumen is proximally coupled to a pressurized fluid control system configured to regulate fluid flow through the elongate tubular member;
   (ii) a tapered recess disposed within the elongate tubular member and near a distal end of the elongate tubular member, the tapered recess having a bottom wall that is non-parallel to a longitudinal axis of the elongate tubular member, a back wall disposed at a distal end of the tapered recess, and a pair of opposing sidewalls extending from a front of the tapered recess to the back wall that enclose an aperture therein; wherein the aperture is disposed near a distal end of the recess in fluid communication with the at least one lumen and within the tapered recess;
   (iii) a nozzle in fluid communication with the aperture, wherein the nozzle is configured to regulate pressurized flow out of the elongate tubular member to manipulate movement of the distal end of the elongate tubular member; and
   transmitting a pressurized fluid from the pressurized fluid control system through the at least one lumen and out of the nozzle.

2. The method of claim 1, wherein the elongate tubular member comprises a plurality of apertures having nozzles disposed near a distal end of the elongate tubular member in fluid communication with the at least one lumen.

3. The method of claim 1, wherein the elongate tubular member comprises a plurality of lumens and a plurality of apertures, wherein each lumen is in fluid communication with each aperture.

4. The method of claim 1, wherein the micro-catheter comprises a flexible distal segment and a semi-rigid proximal segment.

5. The method of claim 1, wherein the micro-catheter further comprises at least one SSID disposed on the distal end of the micro-catheter and at least one lens disposed on a distal end of the SSID.

6. A method of manipulating movement of a micro-catheter within a patient comprising:
   advancing a micro-catheter into a patient, the micro-catheter comprising:
   (i) a closed distal end and at least one lumen therein;
   (ii) first and second tapered recesses disposed near a distal end of the micro-catheter wherein the first tapered recess is disposed distal from the second tapered recess along the longitudinal axis of the micro-catheter;
   (iii) a first aperture disposed within the first tapered recess, the aperture being in fluid communication with the at least one lumen;
   (iv) a second aperture disposed within the second tapered recess, the second aperture being in fluid communication with the at least one lumen; and
   (v) first and second nozzles in fluid communication with the first and second apertures, wherein the nozzles are configured to regulate pressurized flow out of the micro-catheter to manipulate movement of the distal end of the micro-catheter;
   bending a distal portion of the micro-catheter in a controlled manner by creating a first fluid-flow-induced moment force on a distal end of the micro-catheter, wherein the first fluid-flow-induced moment force is created and controlled by injecting a pressure-regulated fluid through the micro-catheter and out of the first aperture; and creating a second fluid-flow-induced moment force by injecting fluid through the second aperture, the direction of the second fluid-flow-induced moment force being different than the direction of first fluid-flow-induced moment force.

7. The method of claim 6, wherein the direction of the second fluid-flow-induced moment force is about opposite the direction of the first fluid-flow-induced moment force.

8. The method of claim 6, wherein the first and second apertures are operatively connected to a single fluid source.

9. The method of claim 6, wherein the first and second recesses are disposed in substantially different directions.

10. The method of claim 6, wherein the direction of the second fluid-flow-induced moment force is non parallel to the first fluid-flow-induced moment force.

11. The method of claim 6, wherein the direction of the second fluid-flow-induced moment force is about opposite the direction of the first fluid-flow-induced moment force.

12. The method claim of 6, wherein the first fluid-flow-induced moment force is greater than the second fluid-flow-induced moment force.

13. The method of claim 6, wherein the direction of fluid flow emanating from the first or second aperture is adjustable.

* * * * *